(12) United States Patent
Goda et al.

(10) Patent No.: US 9,675,502 B2
(45) Date of Patent: Jun. 13, 2017

(54) ABSORBENT ARTICLE

(71) Applicant: UNICHARM CORPORATION, Shikokuchuo-shi, Ehime (JP)

(72) Inventors: Hiroki Goda, Kanonji (JP); Shinichi Ishikawa, Kanonji (JP); Ryota Kawamori, Kanonji (JP); Kengo Ochi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 6 days.

(21) Appl. No.: 14/761,764

(22) PCT Filed: Jan. 17, 2014

(86) PCT No.: PCT/JP2014/050822
§ 371 (c)(1),
(2) Date: Jul. 17, 2015

(87) PCT Pub. No.: WO2014/112590
PCT Pub. Date: Jul. 24, 2014

(65) Prior Publication Data
US 2015/0359687 A1    Dec. 17, 2015

(30) Foreign Application Priority Data
Jan. 18, 2013    (JP) ................................. 2013-007732

(51) Int. Cl.
| *A61F 13/533* | (2006.01) |
| *A61F 13/536* | (2006.01) |
| *A61F 13/539* | (2006.01) |
| *A61F 13/15*  | (2006.01) |
| *A61F 13/537* | (2006.01) |
| *A61F 13/53*  | (2006.01) |
| *A61F 13/534* | (2006.01) |

(52) U.S. Cl.
CPC ...... *A61F 13/536* (2013.01); *A61F 13/15699* (2013.01); *A61F 13/533* (2013.01);
(Continued)

(58) Field of Classification Search
CPC .... A61F 13/533; A61F 13/536; A61F 13/539; A61F 13/15699; A61F 2013/15406;
(Continued)

(56) References Cited

U.S. PATENT DOCUMENTS 3,403,681 A * 10/1968 Hoey ................ A61F 13/15731
156/253
4,840,692 A *  6/1989 Kamstrup-
Larsen .................. A61F 5/4401
156/252

(Continued)

FOREIGN PATENT DOCUMENTS

| EP | 0958801 A1 | 11/1999 |
| JP | 2000-166967 A | 6/2000 |

(Continued)

*Primary Examiner* — Lynne Anderson
(74) *Attorney, Agent, or Firm* — Hauptman Ham, LLP

(57) ABSTRACT

The present invention addresses the problem of providing an absorbent article in which a bonding part for bonding a liquid-permeable layer to an absorbent core has been formed in a low-basis-weight region of the absorbent core and which has all of sufficient flexural rigidity of the bonding part, sufficient bonding strength of the bonding part, and sufficient liquid-absorbing properties. This problem is solved with an absorbent core which comprises a first region that has a given absorbent-material basis weight and second regions (regions 411*a*, 411*b*) that have a lower absorbent-material basis weight than the first region, wherein the ratio of the basis weight of a highly absorbing polymer to the basis weight of the absorbent material in the second regions is regulated to 10/100 to 47/100, and compressed parts are formed inside the second regions.

15 Claims, 6 Drawing Sheets

(52) U.S. Cl.
CPC ...... *A61F 13/539* (2013.01); *A61F 13/53704* (2013.01); *A61F 2013/5349* (2013.01); *A61F 2013/530299* (2013.01); *A61F 2013/530496* (2013.01); *Y10T 156/10* (2015.01)

(58) Field of Classification Search
CPC ........ A61F 2013/530386; A61F 2013/530489; A61F 2013/53051; A61F 2013/53765; A61F 2013/53769; A61F 2013/53782
See application file for complete search history.

(56) References Cited

U.S. PATENT DOCUMENTS

| | | | |
|---|---|---|---|
| 5,030,229 A * | 7/1991 | Yang | .................. A61F 13/47 604/369 |
| 8,134,043 B2 * | 3/2012 | Di Girolamo | ...... A61F 13/4756 604/358 |
| 2003/0187416 A1 | 10/2003 | Shimoe et al. | |
| 2010/0280472 A1 | 11/2010 | Takeuchi et al. | |
| 2012/0059342 A1 | 3/2012 | Kinoshita et al. | |
| 2013/0035656 A1 | 2/2013 | Moriya et al. | |

FOREIGN PATENT DOCUMENTS

| | | |
|---|---|---|
| JP | 2008-178667 A | 8/2008 |
| JP | 2009-207566 A | 9/2009 |
| JP | 2010-233839 A | 10/2010 |
| JP | 2011-177306 A | 9/2011 |
| JP | 2012-148060 A | 8/2012 |
| JP | 2012-239721 A | 12/2012 |
| JP | 2013-9946 A | 1/2013 |
| WO | 2012/090508 A1 | 7/2012 |

* cited by examiner

FIG. 4
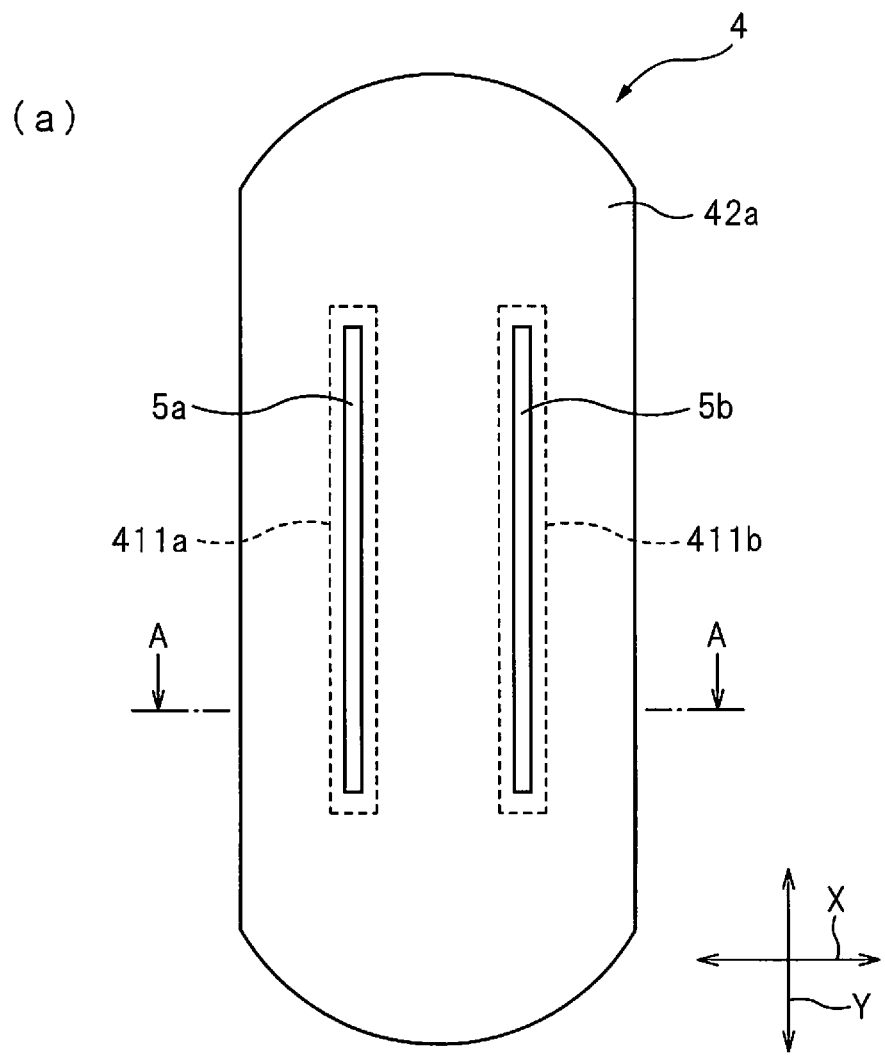
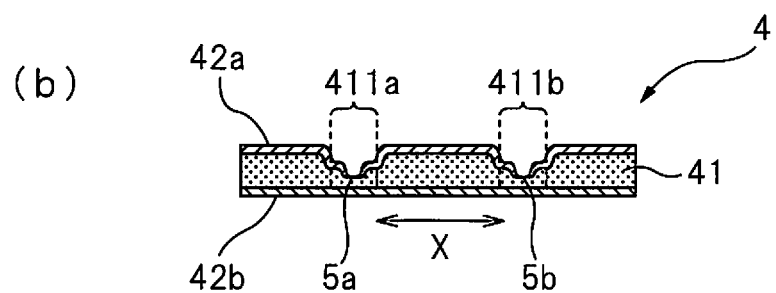

ABSORBENT ARTICLE

RELATED APPLICATIONS

The present application is a National Phase of International Application Number PCT/JP2014/050822, filed Jan. 17, 2014, which claims priority to Japanese Application Number 2013-007732, filed Jan. 18, 2013.

TECHNICAL FIELD

The present invention relates to an absorbent article and a method for producing the same.

BACKGROUND ART

As an absorbent article, one comprising a liquid-permeable top sheet, a liquid-impermeable back sheet, an absorbent body disposed between the top sheet and the back sheet, and a joint section for joining together the top sheet and the absorbent body has been known, wherein the absorbent body has a low basis weight region and a high basis weight region, and wherein the joint section is formed in the low basis weight region (Patent Literature 1). In the absorbent article of Patent Literature 1, the joint section is formed in the low basis weight region in order to reduce the rigidity of the joint section to improve the wearability for the wearer and to prevent liquid from leaking.

CITATION LIST

Patent Literature

Patent Literature 1: Japanese Unexamined Patent Publication No. 2010-233839

SUMMARY OF INVENTION

Problems to be Solved by the Invention

However, the absorbent article described in Patent Literature 1 may possibly cause a decrease in the joining strength of the joint section and a decrease in the liquid absorbability, due to the formation of the joint section in the low basis weight region of the absorbent body.

Accordingly, the present invention is directed to provide an absorbent article comprising a joint section which joins a liquid-permeable layer and an absorbent core, wherein the joint section is formed in a low basis weight region of the absorbent core, and having a sufficient bending flexibility at the joint section, a sufficient joining strength at the joint section, and a sufficient liquid absorbability, as well as a method for producing the same.

Solution to Problem

In order to solve the above problems, the present invention provides an absorbent article comprising a liquid-permeable layer, a liquid-impermeable layer, an absorbent core disposed between the liquid-permeable layer and the liquid-impermeable layer, and a joint section which joins together the liquid-permeable layer and the absorbent core, wherein the absorbent core comprises as absorbent materials a hydrophilic fiber and a superabsorbent polymer, wherein the absorbent core has a first region having a predetermined absorbent material basis weight and a second region having a predetermined absorbent material basis weight which is lower than that of the first region, wherein the ratio of the superabsorbent polymer basis weight to the absorbent material basis weight in the second region is from 10/100 to 47/100, and wherein the joint section is formed inside the second region.

Further, the present invention provides a method for producing the absorbent article of the present invention, comprising the steps of: stacking an absorbent material comprising a superabsorbent polymer at a predetermined weight mixing ratio on the region other than the region where the second region is to be formed, among the region where the absorbent core is to be formed, at a basis weight obtained by subtracting the absorbent material basis weight of the second region from the absorbent material basis weight of the first region, to form a first layer; stacking an absorbent material comprising a superabsorbent polymer at a weight mixing ratio of from 10/100 to 47/100 on the entire region where the absorbent core is to be formed, at the absorbent material basis weight of the second region, to form a second layer; and forming the joint section inside the second region with respect to a laminate comprising the liquid-permeable layer, the second layer and the first layer stacked in this order, or a laminate comprising the liquid-permeable layer, the first layer and the second layer stacked in this order.

Effects of the Invention

According to the present invention, an absorbent article comprising a joint section which joins together a liquid-permeable layer and an absorbent core, wherein the joint section is formed in a low basis weight region of the absorbent core, and having a sufficient bending flexibility at the joint section, a sufficient joining strength at the joint section, and a sufficient liquid absorbability, as well as a method for producing the same are provided.

BRIEF DESCRIPTION OF DRAWINGS

FIG. 4(a) is a plan view of the absorbent body provided in the disposable diaper of FIG. 1, and FIG. 4(b) is a sectional view taken in A-A line in FIG. 4(a).

DESCRIPTION OF EMBODIMENTS

Figure 1:
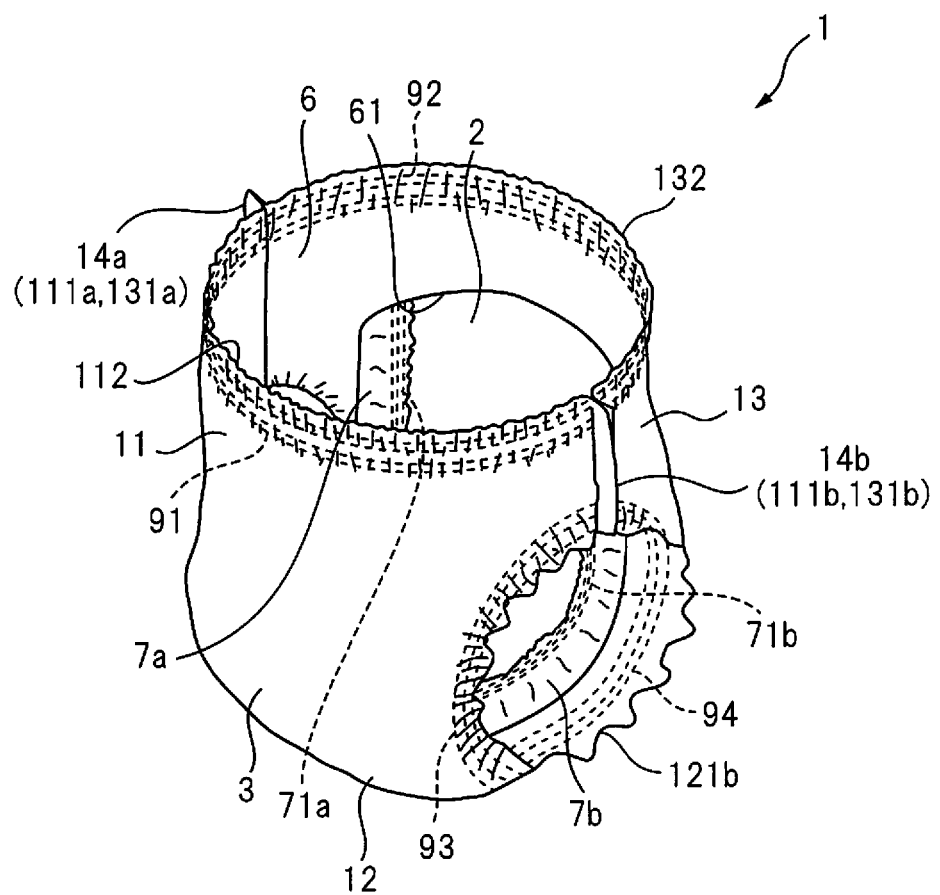
FIG. 1 is a perspective view of a disposable diaper according to an embodiment of the present invention.

An absorbent article and production method of the present invention will be explained below.

[Absorbent Article]

An absorbent article according to one embodiment (Embodiment 1) of the present invention is one which comprises a liquid-permeable layer, a liquid-impermeable layer, an absorbent core disposed between the liquid-permeable layer and the liquid-impermeable layer, and a joint section which joins together the liquid-permeable layer and the absorbent core, wherein the absorbent core comprises as absorbent materials a hydrophilic fiber and a superabsorbent polymer, wherein the absorbent core has a first region having a predetermined absorbent material basis weight and a second region having a predetermined absorbent material basis weight which is lower than that of the first region, wherein the ratio of the superabsorbent polymer basis weight to the absorbent material basis weight in the second region is from 10/100 to 47/100, and wherein the joint section is formed inside the second region.

The absorbent article according to Embodiment 1 has sufficient bending flexibility at the joint section, a sufficient joining strength at the joint section, and a sufficient liquid absorbability (especially, liquid absorbability in the case of repeated absorption of liquid).

The joining strength and bending flexibility of the joint section are associated with the adhesion strength between the hydrophilic fiber and superabsorbent polymer, produced at the joint section. In this regard, in the absorbent article according to embodiment 1, a joint section is formed inside the second region (low basis weight region) having a ratio of the superabsorbent polymer basis weight to the absorbent material basis weight of from 10/100 to 47/100, and therefore the adhesion strength between the hydrophilic fibers and the superabsorbent polymer, produced at the joint section, is sufficient.

The liquid absorbability (especially, liquid absorbability in the case of repeated absorption of liquid) is associated with the mobility of the liquid within the absorbent core. In this regard, in the absorbent article according to embodiment 1, a joint section is formed inside the second region (low basis weight region) having a ratio of the superabsorbent polymer basis weight to the absorbent material basis weight of from 10/100 to 47/100, and therefore the mobility of the liquid within the absorbent core is less susceptible to the restriction by the joint section. That is, the voids in the absorbent core portion where the joint section is formed are expanded by the swelling of the superabsorbent polymer of the predetermined basis weight ratio, as a result of liquid absorption, and therefore the mobility of the liquid at the absorbent core portion is sufficient.

The number of the liquid-permeable layer provided in the absorbent article according to Embodiment 1 is not particularly limited, as long as it is 1 or more. The liquid-permeable layer includes, for example, a top sheet disposed at the skin side (the side with which the skin of the wearer will contact) of the absorbent article, a second sheet disposed between the top sheet and the absorbent core, a core wrap which covers the absorbent core, etc. The liquid-permeable layer with which the absorbent article according to Embodiment 1 may be provided, includes, for example, a top sheet alone, a core wrap alone, a combination of a top sheet and a core wrap, a combination of a top sheet and second sheet, a combination of a top sheet, a second sheet and a core wrap, etc. When the number of the liquid-permeable layer provided in the absorbent article according to Embodiment 1 is 1, the liquid-permeable layer is joined with the absorbent core by the joint section. When the number of the liquid-permeable layer provided in the absorbent article according to Embodiment 1 is 2 or more, one or more of the liquid-permeable layers may be joined with the absorbent core by the joint section. That is, all of the liquid-permeable layers may be joined with the absorbent core by the joint section, or one or more liquid-permeable layers may not be joined with the absorbent core by the joint section. For example, when the absorbent article according to the Embodiment 1 comprises a top sheet and a core wrap as liquid permeable layers, only the core wrap may be joined with the absorbent core by the joint section, or a top sheet and a core wrap may be joined with the absorbent core by the joint section.

In a preferred embodiment (Embodiment 2) of the absorbent article according to Embodiment 1, the absorbent article has a longitudinal direction and a widthwise direction, and the second region has two regions extending in the longitudinal direction of the absorbent article, and the joint section is formed inside each of the two regions. In the absorbent article according to Embodiment 2, two joint sections extending in the longitudinal direction of the absorbent article are formed. In this case, since the mobility of liquid at the absorbent core portion which lies between the two joint sections is susceptible to the restriction by the joint sections, the liquid is easily accumulated at the absorbent core portion, and therefore the liquid absorbed and retained at the absorbent core portion tends to leak out (or to cause rewetting). However, in the absorbent article according to Embodiment 1, the mobility of liquid within the absorbent core is less susceptible to the restriction by the joint section, as described above. Therefore, the effects of the absorbent article according to Embodiment 1 are remarkable in Embodiment 2.

In a preferred embodiment (Embodiment 3) of the absorbent article according to Embodiment 1 or 2, the ratio of the superabsorbent polymer basis weight to the absorbent material basis weight in the second region is 23/100 to 92/100 times the ratio of the superabsorbent polymer basis weight to the absorbent material basis weight in the first region.

In a preferred embodiment (Embodiment 4) of the absorbent article according to any one of Embodiments 1 to 3, the second absorbent material basis weight is from 34/100 to 73/100 times the absorbent material basis weight of the first region.

In a preferred embodiment (Embodiment 5) of the absorbent article according to any one of Embodiments 1 to 4, the liquid-permeable layer comprises a core wrap which covers the absorbent core.

In a preferred embodiment (Embodiment 6) of the absorbent article according to any one of Embodiments 1 to 5, the absorbent article further comprises a liquid-permeable layer which is not joined with the absorbent core by the joint section.

In a preferred embodiment (Embodiment 7) of the absorbent article according to any one of Embodiments 1 to 6, the joint section has a joining strength of 0.065 N/25 mm or more.

In a preferred embodiment (Embodiment 8) of the absorbent article according to any one of Embodiments 1 to 7, the joint section has a flexural rigidity of 9 gf·cm$^2$/cm or less, as determined by KES measurement.

In a preferred embodiment (Embodiment 9) of the absorbent article according to any one of Embodiments 1 to 8, the absorbent article further has an absorption time of 140 seconds or less in the third and fourth droppings when repeating a dropping of 40 mL of an artificial urine four times at a dropping rate of 8 mL/sec. and at 5 minute intervals.

In a preferred embodiment (Embodiment 10) of the absorbent article according to any one of Embodiments 1 to 9, the joint section is a compressed section which integrates the liquid-permeable layer with the absorbent core in a thickness direction.

In the absorbent article of the present invention, two or more embodiments may be combined.

The type and application of the absorbent article of the present invention are not particularly limited. Absorbent articles include, for example, hygiene articles and sanitary articles including disposable diapers, sanitary napkins, panty liners, incontinence pads, sweat sheets, etc., that may be intended for human or for animals such as pet animals, other than human. The liquid to be absorbed by the absorbent article is not particularly limited, and includes, for example, liquid excrements, body fluids, etc., discharged from the wearer.

Hereinafter, one embodiment of the absorbent article of the present invention will be explained with reference to the drawings, taking a disposable diaper as an example.

Figure 2:
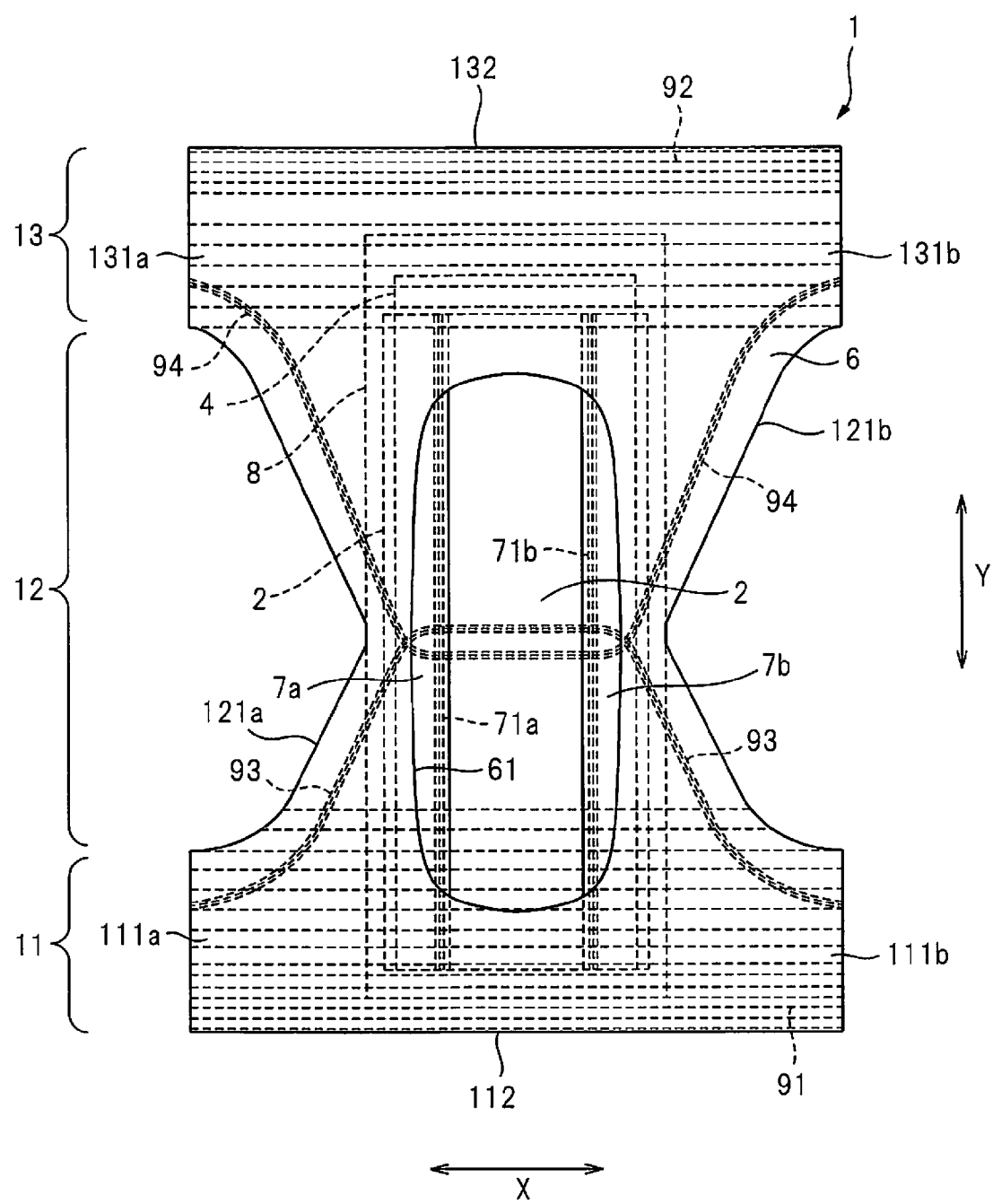
FIG. 2 is a developed plan view showing a state of the disposable diaper of FIG. 1 in which the connection between a front section and a rear section has been released.

As shown in FIGS. 1 and 2, diaper 1 according to one embodiment of the absorbent article of the present invention has front section 11 which contacts the abdominal region of the wearer, intermediate section 12 which contacts the crotch section of the wearer, and rear section 13 which contacts the buttocks and/or back of the wearer. In FIG. 2, the X-axis direction corresponds to the width direction of diaper 1 in the developed state, the Y-axis direction corresponds to the longitudinal direction of diaper 1 in the developed state, and the planar direction extending in the X-axis and Y-axis directions corresponds to the planar direction of diaper 1 in the developed state. This also applies to other Figures.

As shown in FIG. 1, both edges 111a, 111b of front section 11 and both edges 131a, 131b of rear section 13 are joined with each other at joint parts 14a, 14b to form a waist opening defined by edge 112 of front section 11 and edge 132 of rear section 13 and leg openings defined by both edges 121a, 121b of intermediate section 12, and thereby diaper 1 has a pants-type shape.

Figure 3:
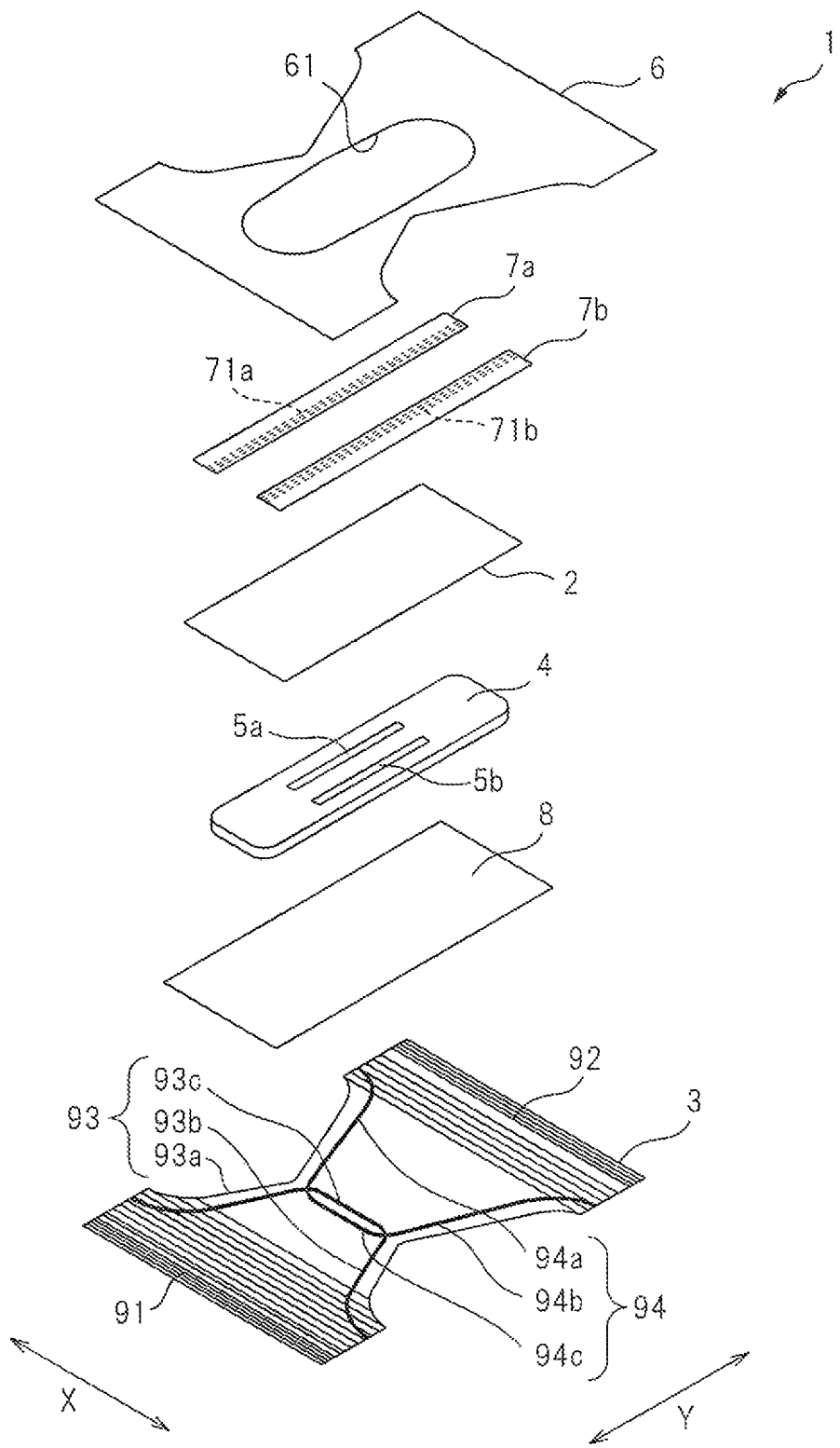
FIG. 3 is an exploded perspective view of the disposable diaper of FIG. 1.

As shown in FIGS. 1 to 3, diaper 1 comprises liquid-permeable top sheet 2, liquid-impermeable back sheet 3, and absorbent body 4 disposed between top sheet 2 and back sheet 3. These members will be explained below.

<Top Sheet>

Top sheet 2 is an example of a liquid-permeable layer which is not joined with the absorbent core by the joint section.

As shown in FIGS. 1 to 3, a portion of top sheet 2 (a portion of the arrangement region of absorbent body 4) is exposed from opening 61 which is formed substantially at the center of cover sheet 6 described later, to form the skin side surface of diaper 1. The arrangement region of absorbent body 4 is a region at which absorbent body 4 overlaps with top sheet 2 when absorbent body 4 is projected to top sheet 2. In this embodiment, the arrangement region of absorbent body 4 is substantially the entire of top sheet 2 (see FIG. 2).

Top sheet 2 is a liquid-permeable sheet through which the liquid excrements of the wearer can permeate. Top sheet 2 includes, for example, a nonwoven fabric, a woven fabric, a synthetic resin film having liquid permeation holes formed therein, a sheet in the form of net having a mesh, etc., and is preferably a nonwoven fabric.

Nonwoven fabrics include, for example, air-through nonwoven fabric, spunbond nonwoven fabric, point-bonded nonwoven fabric, spunlace nonwoven fabric, needle punch nonwoven fabric, melt-blown nonwoven fabric, and combinations thereof (for example, SMS, etc.).

The fibers which constitute the nonwoven fabric include, for example, natural fibers (such as wool, cotton, etc.), regenerated fibers (such as rayon, acetate, etc.), inorganic fibers (such as glass fibers, carbon fibers, etc.), synthetic resin fibers (polyolefins such as polyethylene, polypropylene, polybutylene, ethylene-vinyl acetate copolymer, ethylene-ethyl acrylate copolymer, ethylene-acrylic acid copolymer, ionomer resins, etc.; polyesters such as polyethylene terephthalate, polybutylene terephthalate, polytrimethylene terephthalate, polylactic acid, etc.; and polyamides such as nylon, etc.). The morphology of the fibers which constitute the nonwoven fabric includes conjugate fibers such as core-sheath type fibers, side-by-side-type fibers, island/sea-type fibers, etc.; hollow-type fibers; profiled fibers such as flat fibers, Y-shaped fibers, C-shaped fibers, etc.; latent crimping or actually crimped three-dimensionally crimp fibers; splittable fibers capable of being split by a physical load such as water stream, heat, embossing, etc.

Methods for producing a non-woven fabric include, for example, a method in which a web (fleece) is formed and the fibers are physically or chemically bonded to each other. Methods for forming a web include, for example, spun bond methods, dry methods (carding methods, spunbond methods, meltblown methods, air-laid methods, etc.), wet methods, etc., and the bonding methods include, for example, thermal bonding methods, chemical bonding methods, needle punching methods, stitch bonding methods, spunlace methods, etc. Other than the nonwoven fabrics produced in such manners, a spunlace formed into a sheet form by hydroentangling method may be used as top sheet 2. In addition, a nonwoven fabric having irregularities on the skin-side surface (for example, a nonwoven fabric having on the upperlayer side irregularities formed by contracting the side of the underlayer containing heat-shrinkable fibers, a nonwoven fabric having irregularities formed by applying air during web forming, etc.) may be used as top sheet 2. Forming irregularities in this manner on the skin side surface reduces the contact area between top sheet 2 and the skin.

The thickness, basis weight, density, etc., of top sheet 2 can be appropriately adjusted within a range in which the liquid excrements discharged from the wearer can permeate therethrough. When a nonwoven fabric is used as top sheet 2, the fineness, fiber length and density of the fibers constituting the nonwoven fabric, the basis weight and thickness of the nonwoven fabric, etc., can be appropriately adjusted in view of the permeability to liquid excrements, skin touch, etc.

In view of increasing the concealing property of top sheet 2, an inorganic filler such as titanium oxide, barium sulfate, calcium carbonate, etc., may be added to the nonwoven fabric used as top sheet 2. When the fibers of the nonwoven fabric are core-sheath type conjugate fibers, an inorganic filler may be contained only in the core or may be contained only in the sheath.

<Back Sheet>

Back sheet 3 is an example of the liquid-impermeable layer.

As shown in FIGS. 1 to 3, back sheet 3 constitutes the surface of the clothing side of diaper 1.

Back sheet 3 is a liquid-impermeable sheet capable of preventing the liquid excrements absorbed and retained in absorbent body 4 from leaking. Back sheet 3 includes, for example, waterproof-treated nonwoven fabrics (for example, point-bonded nonwoven fabric, spunbond nonwoven fabric, spunlace nonwoven fabric, etc.), films of synthetic resins (such as polyethylene, polypropylene, polyethylene terephthalate, etc.), composite sheets of a nonwoven fabric and a synthetic resin film.

The thickness, basis weight, density, etc., of back sheet 3 can be appropriately adjusted within a range in which the leakage of the liquid excrements absorbed and retained in absorbent body 4 can be prevented. Back sheet 3 preferably has a gas or moisture permeability as well as liquid impermeability, in order to reduce stuffy feeling during wearing.

<Absorbent Body>

As shown in FIG. 2, absorbent body 4 is disposed extending front section 11 to rear section 13 through intermediate section 12.

As shown in FIGS. 3 and 4, absorbent body 4 comprises absorbent core 41 containing absorbent materials, core wraps 42a, 42b that cover absorbent core 41, and compressed section 5a, 5b that integrate absorbent core 41 with core wrap 42a in the thickness direction of absorbent body 4.

Core wrap 42a is an example of the liquid-permeable layer which is joined to the absorbent core by joint section, and compressed sections 5a, 5b are an example of a joint section for joining together the liquid-permeable layer and the absorbent core.

As shown in FIG. 4, core wrap 42a covers a surface of absorbent core on the side of top sheet 2, and core wrap 42b covers a surface of absorbent core 41 on the side of back sheet 3. Core wraps 42a, 42b prevent absorbent core 41 from being collapsed.

Core wraps 42a, 42b are liquid-permeable sheets through which the liquid excrements of the wearer can permeate. Core wraps 42a, 42b include, for example, a nonwoven fabric, a woven fabric, a synthetic resin film having liquid permeation holes formed therein, a sheet in the form of net having a mesh, etc., and are preferably a nonwoven fabric. The nonwoven fabric includes, for example, those illustrated in connection with top sheet 2.

Although core wraps 42a, 42b are separate members in this embodiment, core wraps 42a, 42b may be a contiguous one piece member. Further, although a portion of the surface of absorbent core 41 is not covered with core wrap 42a, 43 in this embodiment, the entire surface of absorbent core 42 may be covered with core wraps 42a, 43b.

Absorbent core 41 comprises a hydrophilic fiber and a superabsorbent polymer as absorbent materials. In addition to the absorbent materials, absorbent core 41 may optionally comprises additives such as antioxidants, light stabilizers, UV absorbers, neutralizing agents, nucleating agents, epoxy stabilizers, lubricants, antimicrobial agents, flame retardants, antistatic agents, pigments, plasticizers, etc. For example, absorbent core 41 can exhibit functions such as deodorizing effect, antibacterial effect, heat absorption effect, etc. by the incorporation of silver, copper, zinc, silica, activated carbon, aluminosilicate compounds, zeolites, etc.

Hydrophilic fibers include, for example, wood pulps (for example, mechanical pulps such as ground pulp, refiner ground pulp, thermomechanical pulp, chemi-thermomechanical pulp, etc.; chemical pulps such as kraft pulp, sulfide pulp, alkaline pulp, etc.; semichemical pulp, etc.) obtained from softwood or hardwood as a raw material; mercerized pulps obtained by subjecting a wood pulp to a chemical treatment or crosslinked pulps; non-wood pulps such as bagasse, kenaf, bamboo, hemp, cotton (for example, cotton linters), etc.; regenerated fibers such as rayon, fibril rayon, etc.; semisynthetic celluloses such as acetate, triacetate, etc. Among these, ground pulp is preferred, in view of low cost and ease in molding.

Superabsorbent polymer (Superabsorbent Polymer: SAP) includes, for example, superabsorbent polymers of polyacrylic acid salt-based type, polysulfonic acid salt-based type, maleic anhydride salt-based type, polyacrylamide-based type, polyvinyl alcohol-based type, polyethylene oxide-based type, polyaspartic acid salt-based type, polyglutamic acid-based type, polyalginic acid salt-based type, starch-based type, cellulose-based type, etc.; superabsorbent polymers of starch-based type or cellulose-based type, such as starch-acrylic acid (salt) graft copolymers, saponified products of starch-acrylonitrile copolymers, crosslinked products of sodium carboxymethylcellulose, etc., and among these, polyacrylic acid salt-based (particularly sodium polyacrylate-based) superabsorbent polymers are preferred. The shape of the superabsorbent polymer includes, for example, particulate, fibrous, scaly, etc., and in the case of a particulate form, the particle size is preferably from 50 to 1000 µm, and more preferably 100 to 600 µm.

Figure 5:
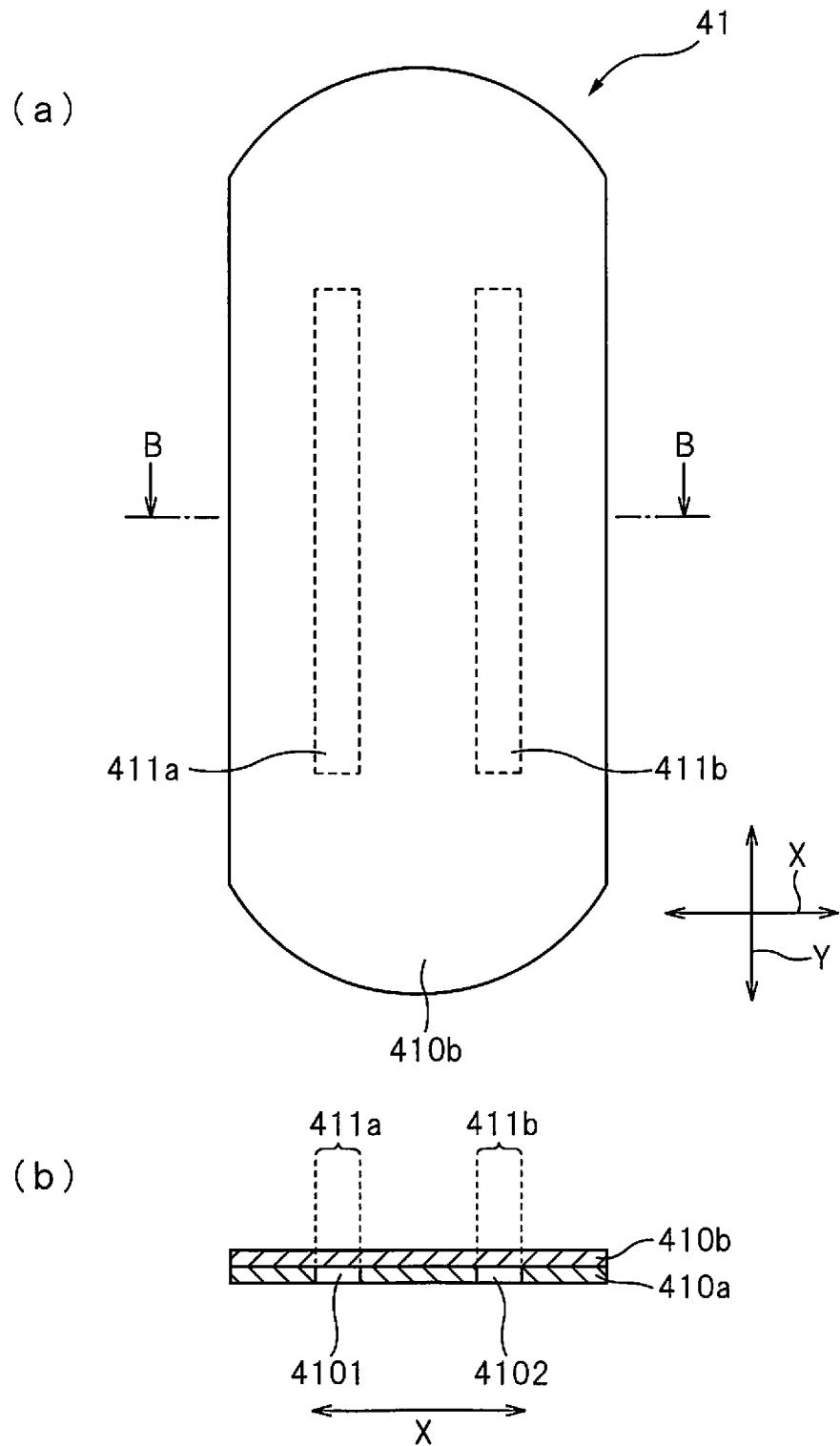
FIG. 5(a) is a plan view of an absorbent core (before the formation of a joint section) provided in the absorbent body of FIG. 4.
FIG. 5(b) is a cross sectional view taken in B-B line in FIG. 5(a).

As shown in FIGS. 4 and 5, absorbent core 41 is partitioned into regions 411a, 411b (corresponding to "the second region" in the absorbent article of the present invention) and the other area (corresponding to "the first region" in the absorbent article of the present invention), when the surface of absorbent core 41 on the side of core wrap 42a is viewed in planar view. Incidentally, absorbent core 41 is partitioned in the same manner when the surface of absorbent core 41 on the side of core wrap 42b is viewed in planar view.

Regions 411a, 411b are low basis weight regions having an absorbent material basis weight lower than that of the other region, and the other region is a region having an absorbent material basis weight higher than those of regions 411a, 411b. The absorbent material basis weight of a given region is calculated as the sum of the basis weights of various absorbent materials contained in that region. The measurement of basis weight can be carried out according to a conventional method. For example, (1) the area to be measured is marked and the surface area thereof: $SA\alpha((m^2)$ is measured; (2) the marked area is cut with a sharp blade, for example, a cutter blade, and the total mass TM (g) is measured; (3) the basis weight $BS\alpha((g/m^2)$ of the area to be measured is determined by the following formula: $BS\alpha((g/m^2)=TM (g)/SA\alpha((m^2)$.

The absorbent material basis weight of the low basis weight regions is preferably from 34/100 to 73/100 times, and more preferably from 34/100 to 55/100 times, the absorbent material basis weight of the high basis weight region. The larger the basis weight difference between the high basis weight region and low basis weight regions within a possible range, the more the bending of the absorbent body is occurred along the low basis weight regions in the widthwise direction, thereby stabilizing the shape of the absorbent body after it is worn, and therefore it is possible to prevent the wearability from being deteriorated due to deformation into an unexpected shape. For example, when the absorbent material basis weight of the higher basis weight region is set to from 300 to 600 $g/m^2$, the absorbent material basis weight of the low basis weight regions may be set to from 102 to 438 $g/m^2$.

The ratio of the superabsorbent polymer basis weight to the absorbent material basis weight in the low basis weight regions (superabsorbent polymer basis weight of the low basis weight regions/absorbent material basis weight of the low basis weight regions) is from 10/100 to 47/100. For example, when the absorbent material basis weight of the low basis weight regions is set to from 102 to 438 $g/m^2$, the superabsorbent material basis weight of the low basis weight regions may be set to from 35 to 319 $g/m^2$. When the ratio of the superabsorbent polymer basis weight to the absorbent material basis weight in the low basis weight regions is less than 10/100, the joining strength of compressed sections 5a, 5b is significantly decreased, and therefore there is a possibility that the deformation, disintegration, fragmentation, or the like, of absorbent body 4 may occur during use of diaper 1, resulting in the leakage of liquid excrement. Also, the ratio of the superabsorbent polymer basis weight to the absorbent material basis weight in the low basis weight regions of less than 10/100 may slow down the movement of the liquid excrement within absorbent core 41, resulting in significant decrease in liquid absorbability (especially, liquid absorbability in the case of repeated absorption of liquid) of absorbent core 41. Whereas when the ratio of the superabsorbent polymer basis weight to the absorbent material basis weight in the low basis weight regions is more than 47/100, the flexural rigidity of compressed sections 5a, 5b is increased significantly, thereby deteriorating the wearability of diaper 1, and therefore there is a possibility that the leakage of liquid excrement may occur.

The lower limit of 10/100 is determined in view of both increasing the joining strength of compressed sections 5a, 5b and improving the liquid absorbability (especially, liquid absorbability in the case of repeated absorption of liquid). The ratio of superabsorbent polymer basis weight to the absorbent material basis weight in the low basis weight regions of 10/100 or more makes it possible to impart compressed sections 5a, 5b with a joining strength of 0.065 N/25 mm or more and to achieve an absorption time of 140 seconds or less in the third and fourth droppings when repeating a dropping of 40 mL of an artificial urine four times at a dropping rate of 8 mL/sec. and at 5 minute intervals.

The joining strength of compressed sections 5a, 5b increases with the increase in the ratio of the superabsorbent polymer basis weight to the absorbent material basis weight in the low basis weight regions, and thereby the liquid absorbability (especially, liquid absorbability in the case of repeated absorption of liquid) is improved. For example, the joining strength of compressed sections 5a, 5b increases with the increase in the ratio of the superabsorbent polymer basis weight to the absorbent material basis weight in the low basis weight regions from 10/100 to 11.8/100, 25/100, 40/100, and 45.5/100, and thereby the liquid absorbability (especially, liquid absorbability in the case of repeated absorption of liquid) is improved. Therefore, the ratios of 10/100, 11.8/100, 25/100, 40/100, and 45.5/100 can have significance as a lower limit, in view of both increasing the joining strength of compressed sections 5a, 5b and improving the liquid absorbability (especially, liquid absorbability in the case of repeated absorption of liquid).

The upper limit of 47/100 is determined in view of decreasing the flexural rigidity of the compressed sections 5a, 5b. The ratio of superabsorbent polymer basis weight to the absorbent material basis weight in the low basis weight regions of 47/100 or less makes it possible to impart compressed sections 5a, 5b with a flexural rigidity of 9 gf·cm$^2$/cm or less.

The flexural rigidity of compressed sections 5a, 5b decreases with the decrease in the ratio of superabsorbent polymer basis weight to the absorbent material basis weight in the low basis weight regions. For example, the flexural rigidity of compressed sections 5a, 5b decreases with the decrease in the ratio of the superabsorbent polymer basis weight to the absorbent material basis weight in the low basis weight regions from 47/100 to 45.5/100, 40/100, 25/100, and 11.8/100. Therefore, the ratios of 47/100, 45.5/100, 40/100, 25/100, and 11.8/100 can have significance as an upper limit, in view of decreasing the flexural rigidity of compressed sections 5a, 5b.

The ratio of the superabsorbent polymer basis weight to the absorbent material basis weight in the low basis weight regions is from 10/100 to 47/100, preferably from 10/100 to 40/100, and more preferably from 12/100 to 35/100, in view of three perspectives, i.e., increasing the joining strength of compressed sections 5a, 5b, decreasing the flexural rigidity of compressed sections 5a, 5b, and improving the liquid absorbability (especially, liquid absorbability in the case of repeated absorption of liquid).

The ratio of the superabsorbent polymer basis weight to the absorbent material basis weight in the high basis weight region (superabsorbent polymer basis weight of the high basis weight region/absorbent material basis weight of the high basis weight region) is preferably from 33/100 to 66/100, and more preferably from 40/100 to 60/100. If the ratio of the hydrophilic fiber is too high, the resulting absorbent body is thick and provides a poor use feeling, whereas if the ratio of the hydrophilic fiber is too low, many cracks may be generated in the absorbent body after liquid absorption, and thereby leading to the deterioration in performance. For example, when the absorbent material basis weight of the high basis weight region is set to from 300 to 600 g/m$^2$, the superabsorbent polymer basis weight of the high basis weight region may be set to from 99 to 396 g/m$^2$.

The superabsorbent polymer ratio of the low basis weight regions (superabsorbent polymer basis weight of the low basis weight regions/absorbent material basis weight of the low basis weight regions) is preferably 23/100 to 92/100 times, and more preferably 33/100 to 66/100 times the superabsorbent polymer ratio of the high basis weight region (superabsorbent polymer basis weight of the high basis weight region/absorbent material basis weight of the high basis weight region).

The thickness and density of absorbent core 41 can be adjusted appropriately depending on the properties required for diaper 1 (for example, absorbability, strength, lightness in weight, etc.). The thickness of the high basis weight region is larger than that of the low basis weight regions, and is typically from 1.0 to 6.0 mm, and preferably from 2.0 to 5.0 mm, and the density of the high basis weight region is higher than the that of the low basis weight regions, and is typically from 0.05 to 0.6 g/cm$^3$, and preferably from 0.06 to 0.3 g/cm$^3$.

In this embodiment, the number of the low basis weight regions of absorbent core 41 is two (regions 411a, 411b), and may be 3 or more.

Region 411a comprises a joint section forming region in which joint section 5a is formed, and a peripheral region surrounding the joint section forming region. Region 411b comprises a joint section forming region in which joint section 5b is formed, and a peripheral region surrounding the joint section forming region.

As shown in FIG. 4, regions 411a, 411b are spaced apart from each other at a constant distance, and extend in the longitudinal direction of absorbent core 41. The distance between regions 411a and 411b (the distance between the center lines of regions 411a and 411b, extending in the longitudinal direction) can be adjusted appropriately depending on the size, etc., of absorbent core 41, and is typically from 20 to 80 mm, and preferably 30 to 60 mm.

As shown in FIGS. 4 and 5, regions 411a, 411b have a substantially linear form. The lengths and widths of regions 411a, 411b can be adjusted appropriately depending on the size, etc., of absorbent core 41. The length is typically from 10 to 600 mm, and preferably from 20 to 400 mm, and the width is typically from 1 to 20 mm, and preferably from 2 to 15 mm.

The position, shape, size, etc., of regions 411a, 411b, are not particularly limited, as long as compressed sections 5a, 5b can be formed inside regions 411a, 411b, and can be adjusted appropriately depending on the positions, shapes, sizes, etc., of compressed sections 5a, 5b to be formed. Although regions 411a, 411b have a substantially linear form in this embodiment, regions 411a, 411b may be partially or entirely curved (for example, in a wavy form, a zigzag form, etc.). Further, the longitudinal end portions of regions 411a, 411b may be connected to with each other to form a ring shape (for example, a circular shape, an elliptical shape, heart-shape, etc.).

The absorbent material basis weight, shape, size, etc., of regions 411a, 411b may be the same or different, and in this embodiment, are substantially the same.

As shown in FIG. 4, compressed section 5a is formed inside of region 411a, and compressed section 5b is formed inside of region 411b.

Compressed sections 5a, 5b are concave sections formed by a heat embossing treatment. In the heat embossing treatment, core wrap 42a and absorbent core 41 are compressed in the thickness direction and are heated. Consequently, compressed sections 5a and 5b that integrate core wrap 42a and absorbent core 41 in the thickness direction of absorbent body 4 are formed as concave sections.

The heat embossing treatment can be carried out by, for example, a process of embossing core wrap 42a and absorbent core 41 by passing them between an embossing roll having patterned protruding parts and a flat roll. In this process, heating during compressing can be effected by heating the embossing roll and/or flat roll. The shapes, arrangement pattern, etc., of the protruding parts of the embossing roll are configured to correspond to the shapes, arrangement pattern, etc., of compressed sections 5a, 5b.

In the embossing treatment, the heating temperature is typically from 80 to 140° C., and preferably from 90 to 120° C., the linear pressure (the pressing force per unit width of the pressed part) is typically from 10 to 200 N/mm, and preferably from 40 to 100 N/mm, and the processing speed is typically from 10 to 500 m/min, and preferably from 20 to 300 m/min.

As shown in FIGS. 3 and 4, compressed sections 5a, 5b are spaced apart from each other at a constant distance, and extend in the longitudinal direction of absorbent body 4. The distance between compressed sections 5a, 5b can be adjusted appropriately depending on the size, etc., of absorbent body 4, and is typically from 20 to 80 mm, and preferably 30 to 60 mm.

As shown in FIGS. 3 and 4, compressed sections 5a, 5b have a substantially linear form. The lengths and widths of compressed sections 5a, 5b can be adjusted appropriately depending on the size, etc., of absorbent core 41. The lengths are typically from 8 to 590 mm, and preferably from 18 to 390 mm, and the widths are typically from 0.5 to 12 mm, and preferably from 1 to 8 mm.

The positions, shapes, sizes, etc., of compressed sections 5a, 5b can be adjusted appropriately depending on the joining strength to be achieved by compressed sections 5a, 5b. Although compressed sections 5a, 5b have a substantially linear form in this embodiment, compressed sections 5a, 5b may be partially or entirely curved (for example, in a wavy form, a zigzag form, etc.). Further, the longitudinal end portions of compressed sections 5a, 5b may be connected to with each other to form a ring shape (for example, a circular shape, an elliptical shape, heart-shape, etc.). In addition, compressed sections 5a, 5b may be formed in the form of dots scattered in a given pattern (for example, a staggered grid pattern, etc.).

Compressed sections 5a, 5b are an example of a joint section which joins together the liquid-permeable layer and the absorbent core. The joint section may be formed by a joining method other than the heat embossing treatment, for example, by a joining method such as ultrasonic embossing, bonding with an adhesive, etc.

The joining strength of compressed section 5a, 5b is preferably 0.065 N/25 mm or more, and more preferably 0.07 N/25 mm or more. The upper limit of the joining strength of compressed sections 5a, 5b is typically 0.5 N/25 mm or more, and preferably 0.4 N/25 mm. The joining strength of compressed sections 5a, 5b of 0.065 N/25 mm or more reduces the deformation, disintegration, fragmentation, or the like, of absorbent body 4 which may occur during use of diaper 1, and consequently absorbent body 4 is maintained in a normal shape, thereby reducing the occurrence of the leakage of liquid excrement.

With respect to the joining strength of compressed sections 5a, 5b, "N/25 mm" means a joining strength (N) per 25 mm width in the planar direction of the interface between core wrap 42a and absorbent core 41, and the planar direction of the interface between core wrap 42a and absorbent core 41 includes, for example, the longitudinal direction (conveyance direction (MD direction) during manufacturing) of absorbent body 4, the widthwise direction (a direction (CD direction) perpendicular to the MD direction) of absorbent body 4, etc., and is preferably the longitudinal direction (MD direction) of absorbent body 4.

The joining strength of compressed sections 5a, 5b can be measured in the following manner. A sample piece (200 mm length×25 mm width) under a standard condition (under a temperature of 20° C. and a humidity of 60%) is mounted in a tensile testing machine (for example, AGS-1kNG manufactured by Shimadzu Corporation) by attaching absorbent core 41 to an upper grip and attaching core wrap 42a to a lower grip at an inter-chuck distance of 25 mm, and applying a load to the sample at a tensile speed of 200 mm/min until core wrap 42a and absorbent core 41 are completely released apart from each other (maximum load) to measure joint strength (N/25 mm) of the compressed sections. In this case, "N/25 mm" means the bonding strength (N) per 25 mm width of the sample piece when the longitudinal direction of the sample piece is taken as the tensile direction.

A sample piece which is used for the measurement of the bonding strength is cut out from absorbent body 4 so as to include a portion of compressed part 5a (or compressed part 5b). In this embodiment, compressed sections 5a, 5b extend in the longitudinal direction of absorbent body 4, and therefore the sample piece may include any part of compressed section 5a (or compressed section 5b). If the compressed sections extend in various directions, as distinct from this embodiment, it is preferred to cut out a sample piece from absorbent body 4 so as to include a portion which extends in the longitudinal direction of absorbent body 4. Further, it is preferred that the longitudinal direction of the sample piece coincides with the extending direction of the compressed section. In this embodiment, a sample piece (for example, 200 mm length×25 mm width) having a longitudinal direction which coincides with the extending direction of compressed section 5a (or compressed section 5b) can be prepared by cutting absorbent body 4 along both sides of compressed section 5a (or compressed section 5b) extending in the longitudinal direction and cutting absorbent body 4 perpendicular to compressed section 5a (or compressed section 5b) extending in the longitudinal direction, and the resulting sample piece can be used in the measurement of the joining strength.

The flexural rigidity of compressed sections 5a, 5b, as determined by the KES (Kawabata Evaluation System) measurement is preferably 9 gf·cm$^2$/cm or less, and more preferably 8 gf·cm$^2$/cm. The lower limit of the flexural rigidity of compressed sections 5a, 5b, as determined by the KES measurement, is typically 2 gf-cm²/cm, and preferably 4 gf-cm²/cm. Due to the flexural rigidity of compressed sections 5a, 5b of 9 gf-cm²/cm or more, as determined by the KES measurement, the wearer can wear diaper 1 without discomfort feeling.

Detailed explanation on the KES measurement is described in the "Standardization and Analysis of Hand Evaluation (2nd ed.)" (author: Sueo Kawabata, published by The Textile Machinery Society of Japan, The hand evaluation measurement and standardization research committee, 1980).

In the KES measurement, a sample piece cut to have a predetermined size (for example, 150 mm length×20 mm width) is gripped by chucks disposed at a predetermined distance (2 cm), and is subjected to pure bending at a constant curvature changing rate in the range of curvature K=0 to 0.3 (cm$^{-1}$), to determine flexural rigidity B per unit length (gf-cm²/cm) from the slope of the M-K curve. Incidentally, M is the bending moment per unit length (gf-cm/cm) of the sample piece. The B value is determined as a slope of the bending moment to the curvature when the sample piece is bent toward the front surface side and the slope become substantially constant.

The KES measurement, for example, may be implemented using KES-FB2-L from Kato Tech Co., Ltd. In doing so, various parameters can be set as follows:
 Measurement mode: half-cycle
 SENS: 2×1
 Chuck distance: 2 cm
 Maximum curvature: 0.5 cm$^{-1}$
 Repeating number: 1
 Flexural Rigidity Value B (g-cm²/cm) is the slope at the curvature K=0.0 to 0.2.

It is preferable that absorbent body 4 has an absorption time of 140 seconds or less in the third and fourth droppings when repeating a dropping of 40 mL of an artificial urine four times at a dropping rate of 8 mL/sec. and at 5 minute intervals. Consequently, liquid excrements rapidly diffuse beyond compressed sections 5a, 5b, thereby preventing the liquid excrements from being concentrated at the introduction part (urination part), and therefore it is possible to provide the wearer with dry feeling.

Core wrap 42a and/or absorbent core 41 may contain a thermoplastic resin fiber. When core wrap 42a and/or absorbent core 41 contains a thermoplastic resin fiber, core wrap 42a and absorbent core 41 can be heat fused together by melting and solidifying the heat-fusible fiber at the time of forming compressed sections 5a, 5b. For example, when the heat-fusible fiber is a composite fiber, core wrap 42a and absorbent core 41 can be heat fused together by melting and solidifying a resin having a low-melting point (for example, the resin of sheath component of a core-sheath conjugate fiber).

The thermoplasic resin fiber is not particularly limited as long as the intersections of the fibers can be heat fused. The thermoplastic resin which constitutes the thermoplastic resin fiber includes, for example, polyolefins, polyesters, polyamides, etc. The polyolefins include, for example, linear low density polyethylene (LLDPE), low density polyethylene (LDPE), medium density polyethylene (MDPE), high density polyethylene (HDPE), polypropylene, polybutylene, copolymers comprising mainly of these components (for example, ethylene-vinyl acetate copolymer (EVA), ethylene-ethyl acrylate copolymer (EEA), ethylene-acrylic acid copolymer (EAA), ionomer resins, etc.). Polyethylenes, particularly HDPE are preferred, since they have a relatively low softening point of about 100° C. and therefore have excellent thermal processing properties as well as a low rigidity and flexible touch. The polyesters include, for example, polyesters of a linear or branched chain polyhydroxy alkanoic acid having carbon atoms of up to 20, including polyethylene terephthalate (PET), poly(trimethylene terephthalate) (PTT), polybutylene terethalate (PBT), polylactic acid, polyglycolic acid, etc., and copolymers comprising mainly of these polyesters, or copolymerized polyesters formed by copolymerizing as a main component an alkylene terephthalate with a minor amount of other components. PET is preferred from the viewpoint of the capability of constituting fibers and nonwoven fabric having high cushioning properties due to having elastic resilience and from the economic viewpoint of industrial availability at a low cost. The polyamides include, for example, 6-Nylon, 6,6-Nylon, etc.

The form of the thermoplastic resin fibers contained in top sheet 2 includes, for example, core-sheath type, side-by-side type, islands/sea type, etc. In view of thermal adhesive properties, conjugate fibers are preferably composed of a core part and a sheath part. The cross sectional shape of the core in the sheath-core type conjugate fibers includes, for example, circular, triangular type, square type, star-shaped, etc., and the core part may be a hollow or may be porous. The cross-sectional area ratio of the core/sheath structure is not particularly limited, but is preferably 80/20 to 20/80, and more preferably 60/40 to 40/60.

The thermoplastic resin fibers may be imparted with a three-dimensional crimped shape. Consequently, even if the fiber orientation is aligned to the planar direction, the buckling strength of the fibers is exerted in the thickness direction, thereby making the fibers harder to crush even if an external force is applied thereto. The three-dimensional crimped shape includes, for example, a zigzag shape, and an omega shape, a spiral shape, etc., and the method for imparting a three-dimensional crimped shape includes, for example, mechanical crimping, shaping by heat shrinking, etc. Mechanical crimping can be controlled by the peripheral speed difference in line speed, heat, pressurization, etc., with respect to continuous linear fibers after spinning, and the greater the number of crimps per unit length of the crimped fibers, the greater the buckling strength of the fibers under external pressure. The number of crimps is typically 5 to 35 per inch, and preferably 15 to 30 per inch. Shaping by heat shrinking can provide a three-dimensional crimping by using the difference in heat shrinking resulted from the melting temperature difference by, for example, heating a fiber comprising two or more resins having different melting points. The cross-sectional shapes of the fibers include, for example, eccentric type, side-by-side type of core-sheath type conjugate fibers. Such fibers have a heat shrinking rate of typically from 5 to 90%, and more preferably from 10 to 80%.

As shown in FIGS. 1 to 3, diaper 1 comprises liquid-impermeable cover sheet 6, liquid-impermeable leakproof cuffs 7a, 7b, liquid-impermeable leakproof sheet 8, elastic members 91, 92, 93, 94, etc., in addition to top sheet 2, back sheet 3 and absorbent body 4. These members will be described below.

<Cover Sheet>

As shown in FIGS. 1 to 3, liquid-impermeable cover sheet 6 is provided on the skin side surface of top sheet 2. As shown in FIGS. 1 to 3, opening 61 is formed in substantially the center of cover sheet 6, and a portion of top sheet 2 (a part of the arrangement region of absorbent body 4) is exposed from opening 61 of cover sheet 6 to form the skin side surface of diaper 1 together with cover sheet 6.

Cover sheet 6 is a liquid-impermeable sheet, and a liquid impermeable sheet includes, for example, a nonwoven fabric which has been subjected to a waterproof treatment (for example, a point bond nonwoven fabric, spun bond nonwoven fabric, a spun lace nonwoven fabric, etc.), a synthetic resin (for example, polyethylene, polypropylene, polyethylene terephthalate, etc.) film, and a composite sheet of a nonwoven fabric and a synthetic resin film, etc.

<Leak-Proof Cuff>

As shown in FIGS. 1 to 3, leak-proof cuffs 7a, 7b each of which is formed of a liquid-impermeable sheet are provided on both sides of opening 61 of cover sheet 6. One end of each of leak-proof cuffs 7a, 7b is a fixed end which is held and fixed between top sheet 2 and cover sheet 6, and the other end is a free end which is exposed from opening 61 of cover sheet 6. The free ends of leak-proof cuffs 7a, 7b are provided with elastic members 71a, 71b extending in the vertical direction Y, and leak-proof cuffs 7a, 7b stand up toward the skin of the wearer.

<Leak-Proof Sheet>

As shown in FIGS. 2 and 3, liquid impermeable leak-proof sheet 8 is provided between back sheet 3 and absorbent body 4. Leak-proof sheet 8 is a liquid-impermeable sheet, and a liquid impermeable sheet includes, for example, a nonwoven fabric which has been subjected to a waterproof treatment (for example, a point bond nonwoven fabric, spun bond nonwoven fabric, a spun lace nonwoven fabric, etc.), a synthetic resin (for example, polyethylene, polypropylene, polyethylene terephthalate, etc.) film, and a composite sheet of a nonwoven fabric and a synthetic resin film, etc.

<Elastic Members>

As shown in FIGS. 1 to 3, elastic members 91, 92, 93, and 94 are provided between back sheet 3 and cover sheet 6 having a hourglass-shape in substantially the same dimensions. Incidentally, a part of elastic members 91, 92, 93 and 94 are omitted in FIG. 1.

As shown in FIG. 1, a waist gather is formed at the waist opening by the elastic shrinkage force of elastic members 91, 92, and leg gathers (leg side cuffs) are formed at the leg openings by the elastic shrinkage force of elastic members 93, 94. Leg gathers prevent the liquid excrement from leaking out from the leg openings.

For example, an elastic body in the form of a strand or string having a thickness of about 310 to 940 dtex can be used as elastic members 91 and 92, and, for example, an elastic body in the form of a strand or string having a thickness of about 470 to 940 dtex can be used as elastic members 93 and 94. A stretchable fibrous nonwoven fabric having elasticity may be used as elastic members 91, 92, 93, and 94.

As shown in FIGS. 2 and 3, a plurality of elastic members 91, 92, are attached in front section 11 and rear section 13, so as to be shrinkable at a stretched state in the transverse direction X, and are spaced apart in longitudinal direction Y. As shown in FIGS. 2 and 3, elastic member 93 comprises parts 93a, 93b that extend along both sides 121a, 121b of intermediate section 12, and part 93c which extends in transverse direction X to connect together parts 93a, 93b. As shown in FIGS. 2 and 3, elastic member 94 comprises parts 94a, 94b that extend along both sides 121a, 121b of intermediate section 12, and part 94c which extends in transverse direction X to connect together parts 94a, 94b. Since absorbent body 4 extends from front section 11 to rear section 13 through intermediate section 12, absorbent body 4 is pressed to the skin side of the wearer by the shrinkage force of elastic members 91, 92, 93, and 94, thereby preventing the wearer's liquid excrement from leaking out.

Diaper 1 is worn so that top sheet 2 and cover sheet 6 are positioned on the inner side (skin-side of the wearer), and back sheet 3 is positioned on the outer side (garment side of the wearer). However, it is not necessary that the wearer wears clothes. The liquid excrement of the wearer penetrates into absorbent body 4 through top sheet 2 exposed from opening 61 of cover sheet 6 and is absorbed and retained by absorbent body 4. Back sheet 3 and leak-proof sheet 6 prevent leakage of the liquid excrements absorbed and held in absorbent body 4 from leaking. The liquid excrement to be absorbed include, for example, urine, menstrual blood, vaginal discharge, etc., and is usually, primarily urine.

In diaper 1, various modifications are possible. Examples of modification of diaper 1 will be explained below.

Modification Example A

In modification example A of diaper 1, top sheet 2 is joined with absorbent core 41 together with wrap 42a by compressed sections 5a, 5b. Top sheet 2 in the modification example A is an example of a liquid-permeable layer which is joined with an absorbent core by the joint sections.

Modification Example B

In modification example B of diaper 1, a liquid-permeable second sheet is disposed between top sheet 2 and absorbent body 4. The second sheet may be or may not be joined with absorbent core 42a together with core wrap 42a. The second seat which is joined with the absorbent core is an example of a liquid-permeable layer which is joined with the absorbent core by the joint section, and the second sheet which is not joined with the absorbent core is an example of a liquid-permeable layer which is not joined with the absorbent core by the joint section.

The second sheet is a liquid-permeable sheet through which the liquid excrements of the wearer can permeate, and includes, for example, a nonwoven fabric, a woven fabric, a synthetic resin film having liquid permeation holes formed therein, a sheet in the form of net having a mesh, etc. and the material, thickness, basis weight, density, etc., can be adjusted appropriately within a range that the liquid excrements of the wearer can permeate through the second sheet.

[Method for Producing Absorbent Article]

The method for producing the absorbent article of the present invention comprises a step of stacking an absorbent material comprising a superabsorbent polymer at a predetermined weight mixing ratio on the region other than the region where the second region is to be formed, among the region where the absorbent core is to be formed, at a basis weight obtained by subtracting the absorbent material basis weight of the second region from the absorbent material basis weight of the first region, to form a first layer; a step of stacking an absorbent material comprising a superabsorbent polymer at a weight mixing ratio of from 10/100 to 47/100 on the entire region where the absorbent core is to be formed, at the absorbent material basis weight of the second region, to form a second layer; and a step of forming the joint section inside the second region with respect to a laminate comprising the liquid-permeable layer, the second layer and the first layer stacked in this order, or a laminate comprising the liquid-permeable layer, the first layer and the second layer stacked in this order.

The method of producing the absorbent article of the present invention is suitable for producing an absorbent article comprising an absorbent core having a high basis weight region (the first region) and a low basis weight region (the second region), wherein the ratio of the superabsorbent polymer basis weight to the absorbent material basis weight in the low basis weight region (the second region) is from 10/100 to 47/100.

When a laminate comprising the liquid-permeable layer, the second layer and the first layer stacked in this order, or a laminate comprising the liquid-permeable layer, the first layer and the second layer stacked in this order is formed, the liquid-permeable layer may be stacked after stacking together the first and second layers, or the first layer may be stacked after stacking together the second layer and the liquid-permeable layer. Further, when the first and second layers are stacked together, the second layer may be formed by stacking an absorbent material on the first layer, and alternatively the first and second layers may be formed separately and then stacked together.

The laminate comprising the liquid-permeable layer, the second layer and the first layer stacked in this order may further have another liquid-permeable layer or a liquid-impermeable layer stacked on the side of the first layer. In this case, another liquid-permeable layer or a liquid-impermeable layer may be stacked on the first layer after stacking together the first layer and the second layer (the second layer may or may not have a liquid-permeable layer stacked thereon), or the second layer (the second layer may or may not have a liquid-permeable layer stacked thereon) may be stacked on the first layer after stacking the first layer and the liquid-permeable layer or liquid-impermeable layer.

The laminate comprising the liquid-permeable layer, the first layer and the second layer stacked in this order may further have another liquid-permeable layer or a liquid-impermeable layer stacked on the side of the first layer. In this case, another liquid-permeable layer or a liquid-impermeable layer may be stacked on the second layer after stacking together the first layer (the second layer may or may not have a liquid-permeable layer stacked thereon) and the second layer, or the first layer (the first layer may or may not have a liquid-permeable layer stacked thereon) may be stacked on the second layer after stacking the second layer and the liquid-permeable layer or liquid-impermeable layer.

One embodiment of the method for producing the absorbent article of the present invention will be explained below, taking as an example a method for producing diaper 1, on the basis of FIG. 6.

[First Step]

The first step is a step of stacking an absorbent material comprising a superabsorbent polymer at a predetermined weight mixing ratio on the region other than the region where low basis weight regions (regions 411a, 411b) are to be formed, among the region where absorbent core 41 is to be formed, at a basis weight obtained by subtracting the absorbent material basis weight of the low basis weight regions (regions 411a, 411b) from the absorbent material basis weight of the high basis weight region (region other that regions 411a, 411b), to form first layer 410a.

Figure 6:
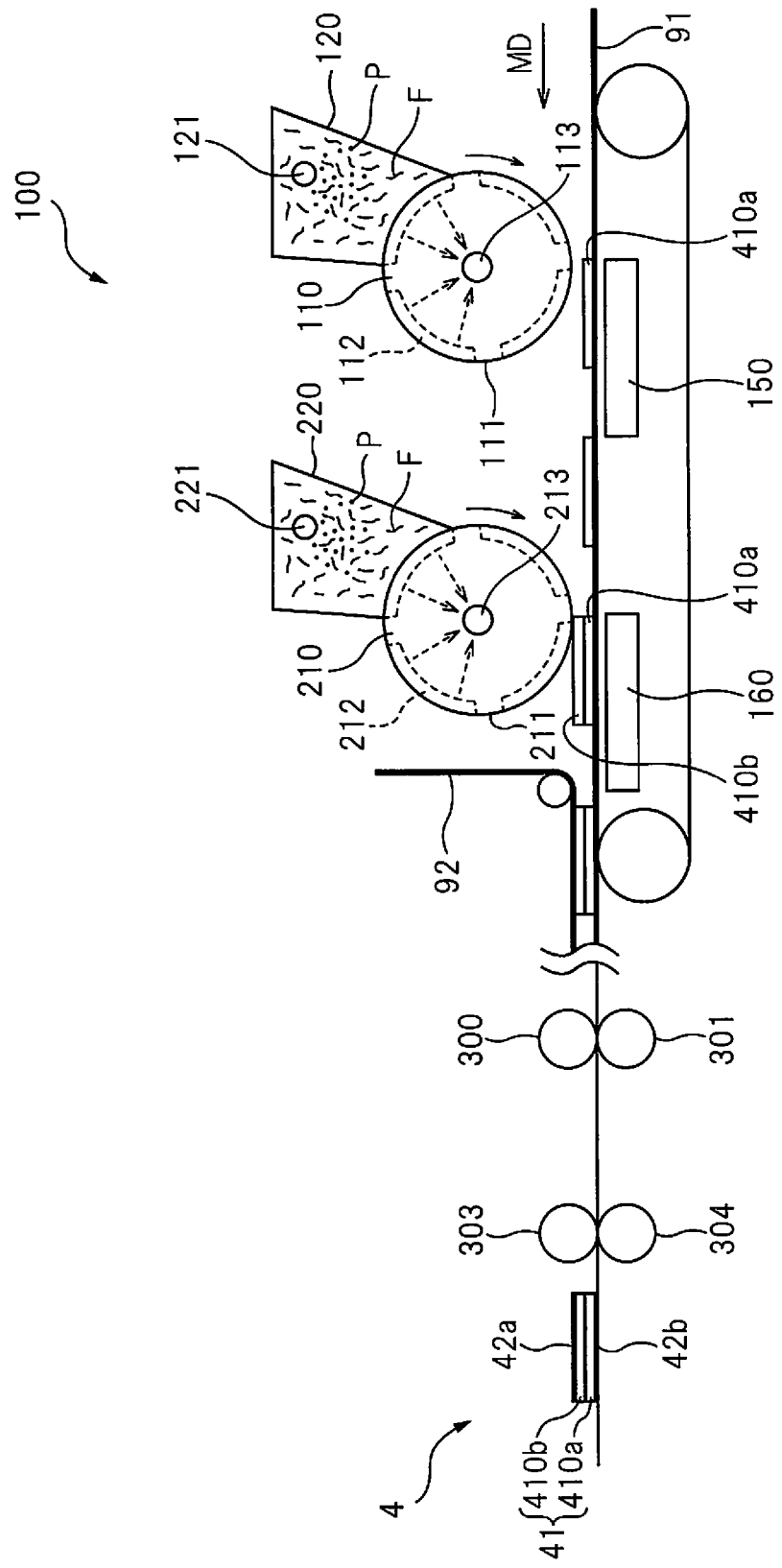
FIG. 6 is a view for explaining the production steps for the absorbent article of FIG. 4.

As shown in FIG. 6, in the formation of the first layer 410a, suction drum 110 which rotates in the conveyance direction MD, and absorbent material feeding unit 120 comprising a hood which covers suction drum 110 are used.

Peripheral surface 111 of suction drum 110 have recessed parts 112 formed thereon at a predetermined pitch in the circumferential direction as molds for filling an absorbent material. When suction drum 110 rotates and recessed parts 112 enter into absorbent material feeding unit 120, suction unit 113 acts on recessed parts 112 and the absorbent material fed from absorbent material feeding unit 120 is vacuum sucked into recessed parts 112. The absorbent material which is fed from the absorbent material feeding unit 120 comprises hydrophilic fibers F fed from the grinder (not shown) and superabsorbent polymer particles P fed from particle feeing section 121 at a predetermined weight mixing ratio. The weight mixing ratio of the superabsorbent polymer to the absorbent material (hydrophilic fibers F+superabsorbent polymer particles P) is preferably 33/100 to 66/100, and more preferably 40/100 to 60/100.

The bottom of recessed parts 112 is in the form of a mesh and is provided with a number of through-holes. The suction unit 113 exerts a suction action against recessed parts 112 through these through-holes. Recessed parts 112 are provided with two non-breathable protrusions extending in the longitudinal direction at a constant distance, and these non-breathable protrusions are configured so that the suction action of suction unit 113 does not act on these non-breathable protrusions.

In this manner, the first layer 410a is formed in recessed parts 112. The first layer 410a contains hydrophilic fibers F and superabsorbent polymer particles P in a mixed state. As shown in FIG. 5, the first layer 410a has cavities 4101, 4102 corresponding to the two non-breathable protrusions, and the other portion has a constant thickness.

The first layer 410a which is formed in recessed part 112 is transferred onto lower core wrap 91 traveling toward the conveyance direction MD by the action of transfer sunction unit 150. A hot melt adhesive has been applied on the upper surface of lower core wrap 91, and the first layer 410a is bonded to the lower core wrap 91 by the hot melt adhesive. Lower core wrap 91 onto which the first layer 410a has been transferred travels toward the conveyance direction MD.

[Second Step]

The second step is a step of stacking an absorbent material comprising a superabsorbent polymer at a weight mixing ratio of from 10/100 to 47/100 on the entire region where absorbent core 41 is to be formed, at the absorbent material basis weight of the low basis weight regions (regions 411a, 411b), to form a second layer 410b.

In the formation of the second layer 410b, suction drum 210 which rotates in the conveyance direction MD, and absorbent material feeding unit 220 comprising a hood which covers suction drum 210 are used.

Peripheral surface 211 of suction drum 210 have recessed parts 212 formed thereon at a predetermined pitch in the circumferential direction as molds for filling an absorbent material. When suction drum 210 rotates and recessed parts 212 enter into absorbent material feeding unit 220, suction unit 213 acts on recessed parts 212 and the absorbent material fed from absorbent material feeding unit 220 is vacuum sucked into recessed parts 212. The absorbent material which is fed from the absorbent material feeding unit 220 comprises hydrophilic fibers F fed from the grinder (not shown) and superabsorbent polymer particles P fed from particle feeing section 221 at a predetermined weight mixing ratio. The weight mixing ratio of the superabsorbent polymer to the absorbent material (hydrophilic fibers F+superabsorbent polymer particles P) is preferably 33/100 to 66/100, and more preferably 40/100 to 60/100.

The bottom of recessed parts 212 is in the form of a mesh and is provided with a number of through-holes. The suction unit 213 exerts a suction action against recessed parts 212 through these through-holes.

In this manner, the second layer 410b is formed in recessed parts 212. The second layer 410b contains hydrophilic fibers F and superabsorbent polymer particles P in a mixed state. As shown in FIG. 5, the second layer 410b has a substantially constant thickness.

The second layer 410b which is formed in the recessed part 212 is transferred onto lower core wrap 91 traveling toward the conveyance direction MD by the action of transfer sunction unit 160. Lower core wrap 91 on which the first layer 410a and the second layer 410b have been stacked in this order travels toward the conveyance direction MD, and then upper core wrap 92 is stacked on the second layer 410b. A hot melt adhesive has been applied on the bottom surface of upper core wrap 92, and the second layer 410b is bonded to the upper core wrap 92 by the hot melt adhesive.

Thus, a continuous body of a laminate comprising the upper core wrap 92, the second layer 410b, the first layer 410a and the lower core wrap 91 stacked in this order is formed. This continuous body is cut out into a predetermined shape by a pair of rolls 300, 301 to form individual laminates comprising core wrap 42a, the second layer 410b, the first layer 410a and core wrap 42b stacked in this order.

As shown in FIG. 5, absorbent core 41 is comprised of the first layer 410a and the second layer 410b, and absorbent core 41 is partitioned into regions 411a, 411b (corresponding to "the second region" in the absorbent article of the present invention) and the other area (corresponding to "the first region" in the absorbent article of the present invention), when the surface of absorbent core 41 on the side of core wrap 42a is viewed in planar view. Incidentally, absorbent core 41 is partitioned in the same manner when the surface of absorbent core 41 on the side of core wrap 42b is viewed in planar view.

Regions 411a, 411b are low basis weight regions having an absorbent material basis weight lower than that of the other region by the presence of cavities 4101, 4102 of the first layer 410a.

[Third Step]

The third step is a step of forming compressed sections 5a, 5b inside the low basis weight regions (regions 411a, 411b), with respect to a laminate comprising core wrap 42a, the second layer 410b, the first layer 410a and core wrap 42b stacked in this order. A pair of rolls 303, 304 is used in the formation of compressed sections 5a, 5b.

Roll 303 is an upper roll having protruding parts (not shown) on the outer peripheral surface thereof, and roll 304 is a lower roll having a smooth outer peripheral surface. The protruding parts of roll 303 are formed so as to correspond to the shape, arrangement pattern, etc., of compressed sections 5a, 5b, and core wrap 42a and absorbent core 41 are compressed in the thickness direction and are heated by these protruding parts. Consequently, compressed sections 5a, 5b that integrate core wrap 42a and absorbent core 41 in the thickness direction are formed as concave sections. Compressed sections 5a, 5b formed in this manner are densified, and have a thickness smaller than that of the other sections and a density higher than that of the other sections.

Rolls 303 and/or 304 may be heated to carry out heating during compressing. In the embossing treatment with rolls 303, 304, the heating temperature is typically 80 to 140° C., and preferably 90 to 120° C., the linear pressure (the pressing force per unit width of the pressed part) is typically from 10 to 200 N/mm, and preferably from 40 to 100 N/mm, and the processing speed is typically from 10 to 500 m/min, and preferably from 20 to 300 m/min.

In this manner, absorbent body 4 having absorbent core 41 containing an absorbent material, core wraps 42a, 42b that cover absorbent core 41, and compressed sections 5a, 5b that integrate absorbent core 41 and core wrap 42a in the thickness direction of absorbent body 4 is formed.

[Other Steps]

Production of diaper 1 using absorbent body 4 can be carried out according to a conventional method.

EXAMPLES

Examples 1 to 4 and Comparative Examples 1 to 6

(1) Production of Absorbent Core

A mixture of fluff pulp (Super Soft from International Paper Co.) and a superabsorbent polymer (UG860 from Sumitomo Seika Chemicals Co., Ltd.) (hereinafter referred to as "SAP") was used as an absorbent material to produce an absorbent core having a structure shown in FIG. 5. In Examples 1 to 4 and Comparative Examples 1 to 5, the size of the absorbent core was set to 400 mm length×140 mm width, the size of the low basis weight region was set to 220 mm length×7 mm width, the number of the low basis weight regions is set to 2, and the distance between the low basis weight regions (the distance between the center lines of the low basis weight regions, extending in the longitudinal direction) was set to 50 mm. In Comparative Example 6, the size of the low basis weight region was changed to 220 mm length×3 mm width (the other conditions are the same as those of Examples 1 to 4 and Comparative Examples 1 to 5).

In the production of the absorbent core, stacking an absorbent material on the region other than two regions (each is 220 mm length×7 mm width in Examples 1 to 4 and Comparative Examples 1 to 5, and each is 220 mm length×3 mm width in Comparative Example 6) where low basis weight regions are to be formed, among the region (400 mm length×140 mm width) where the absorbent core is to be formed, at a basis weight obtained by subtracting the basis weight (see Table 1) of the low basis weight region from the basis weight (see Table 1) of the high basis weight region, to form a first layer (the first layer 410a in FIG. 5). In the first layer, the two regions where low basis weight regions are to be formed are cavities (cavities 4101, 4102 in FIG. 5).

Then, an absorbent material is stacked on the entire region where the absorbent core is to be formed at a basis weight of the low basis weight region (see Table 1) to form the second layer (the second layer 410b in FIG. 5) on the first layer.

The pulp basis weight and SAP basis weight of the high basis weight regions and low basis weight regions in Examples 1 to 4 and Comparative Examples 1 to 5 are as shown in Table 1.

TABLE 1

| | High basis weight region | | | Low basis weight region | | | | | Embossed portion | |
| --- | --- | --- | --- | --- | --- | --- | --- | --- | --- | --- |
| | Total basis weight (g/m²) | Pulp basis weight (g/m²) | SAP basis weight (g/m²) | Total basis weight (g/m²) | Pulp basis weight (g/m²) | SAP basis weight (g/m²) | SAP ratio (%) | Width (mm) | Presence or absence | Width (mm) |
| Example 1 | 500 | 250 | 250 | 275 | 150 | 125 | 45.5% | 7 | Present | 3 |
| Example 2 | 500 | 250 | 250 | 250 | 150 | 100 | 40.0% | 7 | Present | 3 |
| Example 3 | 500 | 250 | 250 | 200 | 150 | 50 | 25.0% | 7 | Present | 3 |
| Example 4 | 500 | 250 | 250 | 170 | 150 | 20 | 11.8% | 7 | Present | 3 |

TABLE 1-continued

| | High basis weight region | | | Low basis weight region | | | | | Embossed portion | |
| --- | --- | --- | --- | --- | --- | --- | --- | --- | --- | --- |
| | Total basis weight (g/m²) | Pulp basis weight (g/m²) | SAP basis weight (g/m²) | Total basis weight (g/m²) | Pulp basis weight (g/m²) | SAP basis weight (g/m²) | SAP ratio (%) | Width (mm) | Presence or absence | Width (mm) |
| Comp. Example 1 | 400 | 400 | 0 | 100 | 100 | 0 | 0.0% | 7 | Present | 3 |
| Comp. Example 2 | 500 | 250 | 250 | 500 | 250 | 250 | 50.0% | 7 | Present | 3 |
| Comp. Example 3 | 500 | 250 | 250 | 300 | 150 | 150 | 50.0% | 7 | Present | 3 |
| Comp. Example 4 | 500 | 250 | 250 | 150 | 150 | 0 | 0.0% | 7 | Present | 3 |
| Comp. Example 5 | 500 | 250 | 250 | 250 | 150 | 100 | 40.0% | 7 | Absent | — |
| Comp. Example 6 | 500 | 250 | 250 | 250 | 150 | 100 | 40.0% | 3 | Present | 3 |

(2) Production of Absorbent Body

An absorbent core was disposed between two core wraps (hydrophilic SMS nonwoven fabrics having a basis weight of 10 g/m² from CNC Co., Ltd.) that have been coated with a hot-melt adhesive (MQ633E from Henkel Corporation) (at a coating basis weight of 5 g/m²) in advance, and the high basis weight region was compressed to a predetermined thickness (3 mm) with a pressing equipment (pressing under a load of 23 kN for 2 seconds). In the measurement of the thickness, a thickness gauge having a sample (dial thickness gauge, large type, J-B type, the probe specification ϕ50 mm, from Ozaki Seisakusho Co.) was used, and an average value of the thicknesses of ten sample pieces (50 mm×50 mm) was calculated.

Subsequently, embossed portions were formed with an embossing press machine. However, embossed portion was not formed in Comparative Example 5. The embossed portions were formed in the two low basis weight regions of the absorbent core. An embossing treatment was carried out using an embossing plate having protruding parts thereon (heating temperature 90° C.), and a flat plate thereon (heating temperature 90° C.) as a lower plate. Embossing time was 3 seconds, and embossing pressure was 30 N/mm². Embossed portions (200 mm length×3 mm width×0.3 mm depth), extending in the longitudinal direction of the nonwoven fabric when the upper nonwoven fabric was viewed in planar view, were formed by the embossing treatment. Incidentally, the embossed portions were formed so that the center lines thereof coincide with the center lines of the low basis weight regions.

(3) Measurement of Flexural Rigidity of the Absorbent Body

The absorbent body prepared in (2) was cut along both sides of an embossed portion extending in the longitudinal direction of the absorbent body, and was cut perpendicular to the extending direction of the embossed portion to prepare a sample piece of 150 mm length×20 mm width. The length of the sample is the length in the direction that the sample is inserted into the chuck of the measurement device.

The sample piece under standard conditions (under an atmosphere of a temperature of 20° C. and a humidity of 60%) was set on a measurement device (Large Pure Bending Tester KES-FB2-L from Kato Tech Co., ltd.), and flexural rigidity value B (gf-cm²/cm) according to KES measurement was calculated.

The measurement parameters were set as follows.
Measurement mode: half-cycle
SENS: 2×1
Sample gripping distance: 2 cm
Maximum curvature: 0.5 cm$^{-1}$
Repeating number: 1
Bending rigidity value B (g-cm²/cm) is the slope at the curvature K=0.0 to 0.2.

B value (g-cm²/cm) was measured five times, and an average value was determined. The higher the B value, the higher the flexural rigidity.

(4) Measurement of Joining Strength of the Embossed Portion

The absorbent body prepared in (2) was cut along both sides of an embossed portion extending in the longitudinal direction of the absorbent body, and was cut perpendicular to the extending direction of the embossed portion to prepare a sample piece of 200 mm length×25 mm width.

The sample piece under standard conditions (under an atmosphere of a temperature of 20° C. and a humidity of 60%) was mounted on a tensile testing machine (table-top precision universal testing machine AGS-1kNG from Shimadzu Corporation) by attaching absorbent core to an upper grip and attaching core wrap to a lower grip at a gripping distance of 25 mm. A load (maximum load) was applied to the sample at a tensile speed of 200 mm/min until the core wrap and the absorbent core are completely released apart from each other to measure joint strength (N) of the embossed portions per 25 mm width of the sample piece when the longitudinal direction of the sample piece is taken as the tensile direction.

The measurement parameters were set as follows.
Load cells used: 50 N
Distance between chucks: 25 mm
Test type: peel
Test force polarity: Standard
Testing force direction: up
Sampling time duration: 50 m sec
First half deleting range: 25 mm displacement
Second half deleting range: 175 mm displacement
Joining strength (N/25 mm) was measured five times, and an average value was determined.

(5) Measurement of Absorption Time of Artificial Urine

The absorbent body prepared in (2) above was placed on a horizontal surface, and a cylinder was placed on the central portion of the absorbent body. A cylinder made of a transparent plastic, having an inner diameter of 30 mm, outer diameter 35 mm, and a total length of 230 mm was used as the cylinder. An iron sleeve having an inner diameter which is adapted to the outer diameter of the cylinder was used to adjust the weight to 325 g.

The tip of the buret was fixed at the position 10 mm below from the top end of the cylinder upper end.

Forty milliliters of an artificial urine was dropped at a dropping rate (the first time), and the time from the initiation of dropping until the artificial urine in the cylinder was consumed was measured. The artificial urine was prepared by adding 200 g of urea, 80 g of sodium chloride, 8 g of magnesium sulfate heptahydrate, 3 g of calcium chloride dihydrite, and 1 g of dye Blue No. 1, to 10 kg of ion-exchanged water, and stirring them well.

After 5 minutes from the initiation of the first dropping, 40 mL of the artificial urine was dropped (second time) at a dropping rate of 8 mL/sec, and the time from the initiation of the second dropping until the artificial urine in the cylinder was consumed was measured.

After 10 minutes from the initiation of the first dropping, 40 mL of the artificial urine was dropped (third time) at a dropping rate of 8 mL/sec, and the time from the initiation of the third dropping until the artificial urine in the cylinder was consumed was measured.

After 15 minutes from the initiation of the first dropping, 40 mL of the artificial urine was dropped (fourth time) at a dropping rate of 8 mL/sec, and the time from the initiation of the fourth dropping until the artificial urine in the cylinder was consumed was measured.

Each sample was measured for n=3 times to obtain a mean value.

(6) Result

The results will be shown in Table 2.

TABLE 2

| | Repeated absorption rate (sec) | | | | Peel | KES large |
| | First time | Second time | Third time | Fourth time | strength (N/25 mm) | bending (gf-cm²/cm) |
| --- | --- | --- | --- | --- | --- | --- |
| Example 1 | 38.4 | 70.9 | 87.0 | 91.3 | 0.0912 | 8.412 |
| Example 2 | 40.3 | 83.5 | 112.9 | 114.2 | 0.0900 | 8.005 |
| Example 3 | 44.8 | 103.7 | 123.1 | 128.4 | 0.0716 | 7.905 |
| Example 4 | 47.8 | 113.4 | 130.7 | 137.1 | 0.0692 | 6.754 |
| Comp. Example 1 | 48.1 | 71.3 | 74.8 | 76.3 | 0.0481 | 11.359 |
| Comp. Example 2 | 45.4 | 66.5 | 90.0 | 95.4 | 0.0801 | 10.285 |
| Comp. Example 3 | 36.4 | 58.4 | 73.4 | 82.7 | 0.0825 | 9.315 |
| Comp. Example 4 | 59.2 | 133.6 | 149.7 | 154.6 | 0.0625 | 5.393 |
| Comp. Example 5 | 29.2 | 63.6 | 83.7 | 86.6 | 0.0052 | 2.254 |
| Comp. Example 6 | 39.3 | 82.0 | 109.8 | 111.4 | 0.0940 | 9.201 |

In view of the durability, texture, performance and the like, required in commodities, the following criterions have been set.

[Criterion 1] The embossed portion has a joining strength of 0.65 N/25 mm or more.
[Criterion 2] The embossed portion has a flexural rigidity of 9 gf-cm²/cm or less, as determined KES measurement.
[Criterion 3] The absorption time in the third and fourth droppings is 140 seconds or less in the third and fourth droppings when repeating a dropping of 40 mL of an artificial urine four times at a dropping rate of 8 mL/sec. and at 5 minutes intervals.

Examples 1 to 4 satisfied all the criterions. However, Comparative Examples 1 to 5 did not satisfy one or more criterions.

EXPLANATION OF SYMBOLS

1 Disposable diaper (absorbent article)
2 Top sheet (liquid-permeable layer which is not joined with an absorbent core by a joint section)
3 Back sheet (liquid-impermeable layer)
4 Absorbent body
41 Absorbent core
42a Core wrap (liquid-permeable layer which is joined with the absorbent core by a joint section)
411a Low basis weight region (the second region having an absorbent material basis weight lower than that of the first region)
411b Low basis weight region (the second region having an absorbent material basis weight lower than that of the first region)

The invention claimed is:

1. An absorbent article comprising:
a first liquid-permeable layer,
a liquid-impermeable layer,
a second liquid-permeable layer,
an absorbent core disposed between the first liquid-permeable layer and the liquid-impermeable layer, and
a joint section joining the first liquid-permeable layer and the absorbent core,
wherein the absorbent core includes absorbent materials having a hydrophilic fiber and a superabsorbent polymer,
wherein the absorbent core has a first region having a predetermined absorbent material basis weight and a second region having a predetermined absorbent material basis weight which is lower than that of the first region,
wherein a ratio of a superabsorbent polymer basis weight to the predetermined absorbent material basis weight in the second region is from 10/100 to 47/100,
wherein the joint section is formed inside the second region,
wherein the second liquid-permeable layer is not joined with the absorbent core by the joint section, and
wherein the ratio of the superabsorbent polymer basis weight to the predetermined absorbent material basis weight in the second region is 23/100 to 92/100 times a ratio of the superabsorbent polymer basis weight to the predetermined absorbent material basis weight in the first region.

2. The absorbent article of claim 1, wherein
the absorbent article has a longitudinal direction and a widthwise direction,
the second region has two regions each extending in the longitudinal direction of the absorbent article, and
the joint section is formed in each of the two regions.

3. The absorbent article of claim 2, wherein the predetermined absorbent material basis weight of the second region is from 34/100 to 73/100 times the predetermined absorbent material basis weight of the first region.

4. The absorbent article of claim 2, wherein the first liquid-permeable layer comprises a core wrap which covers the absorbent core.

5. The absorbent article of claim 2, wherein the joint section has a joining strength of 0.065 N/25 mm or more.

6. The absorbent article of claim 2, wherein the joint section has a flexural rigidity of 9 gf·cm2/cm or less, as determined by KES measurement.

7. The absorbent article of claim 2, having an absorption time of 140 seconds or less in the third and fourth droppings when repeating a dropping of 40 mL of artificial urine four times at a dropping rate of 8 mL/sec. and at 5 minute intervals.

8. The absorbent article of claim 2, wherein the joint section is a compressed section which integrates the first liquid-permeable layer with the absorbent core in a thickness direction.

9. The absorbent article of claim 1, wherein the predetermined absorbent material basis weight of the second region is from 34/100 to 73/100 times the predetermined absorbent material basis weight of the first region.

10. The absorbent article of claim 1, wherein the first liquid-permeable layer comprises a core wrap which covers the absorbent core.

11. The absorbent article of claim 1, wherein the joint section has a joining strength of 0.065 N/25 mm or more.

12. The absorbent article of claim 1, wherein the joint section has a flexural rigidity of 9 gf·cm$^2$/cm or less, as determined by KES measurement.

13. The absorbent article of claim 1, having an absorption time of 140 seconds or less in the third and fourth droppings when repeating a dropping of 40 mL of artificial urine four times at a dropping rate of 8 mL/sec. and at 5 minute intervals.

14. The absorbent article of claim 1, wherein the joint section is a compressed section which integrates the first liquid-permeable layer with the absorbent core in a thickness direction.

15. A method for producing the absorbent article of claim 1, comprising the steps of:
   stacking an absorbent material comprising a superabsorbent polymer at a predetermined weight mixing ratio, on a region other than the region where the second region is to be formed, among a region where the absorbent core is to be formed, at a basis weight obtained by subtracting the predetermined absorbent material basis weight of the second region from the predetermined absorbent material basis weight of the first region, to form a first layer;
   stacking an absorbent material comprising a superabsorbent polymer at a weight mixing ratio of from 10/100 to 47/100 on an entirety of the region where the absorbent core is to be formed, at the predetermined absorbent material basis weight of the second region, to form a second layer; and
   forming the joint section in the second region with respect to
      a laminate comprising the first liquid-permeable layer, the second layer, and the first layer stacked in this order, or
      a laminate comprising the first liquid-permeable layer, the first layer, and the second layer stacked in this order.

* * * * *